United States Patent [19]

Calbick et al.

[11] Patent Number: 5,260,485
[45] Date of Patent: Nov. 9, 1993

[54] PROCESS OF MAKING ALKYL PHOSPHINE COMPOUNDS BY REACTING AN OLEFIN AND A PHOSPHINE IN THE VAPOR PHASE OVER A MINERAL ACID CATALYST

[75] Inventors: C. Joseph Calbick, Weston, Conn.; Mark A. Kuck, Upper Montclair, N.J.; Donald H. Valentine, Ridgefield, Conn.

[73] Assignee: American Cyanamid Company, Stamford, Conn.

[21] Appl. No.: 848,504

[22] Filed: Mar. 9, 1992

Related U.S. Application Data

[63] Continuation-in-part of Ser. No. 728,502, Jul. 11, 1991, abandoned.

[51] Int. Cl.$^5$ .............................................. C07F 9/50
[52] U.S. Cl. ...................................................... 568/8
[58] Field of Search ............................................ 568/8

[56] References Cited

U.S. PATENT DOCUMENTS

| | | | |
|---|---|---|---|
| 2,584,112 | 2/1952 | Brown | 260/607 |
| 3,352,925 | 11/1967 | Hamilton | 568/8 |
| 4,163,760 | 8/1979 | Elsner et al. | 260/606.5 P |
| 4,368,098 | 1/1983 | Manasevit | 156/606 |
| 4,404,265 | 9/1983 | Manasevit | 428/689 |
| 4,857,655 | 8/1989 | Valentine | 556/70 |
| 4,922,025 | 5/1990 | Hoelderich et al. | 568/8 |

Primary Examiner—Marianne M. Cintins
Assistant Examiner—Michael B. Hydorn
Attorney, Agent, or Firm—Frank M. Van Riet

[57] ABSTRACT

Alkylphosphines are made by a reaction of gaseous phosphine and the corresponding gaseous olefin in contact with at least one non-oxidizing acid catalyst. Products produced thereby are alkylphosphines which contain substantially no metallic or oxygenating impurities. The process is a continuous process and employs a mineral acid catalyst either in solid form or as a liquid supported on a solid, inert material.

5 Claims, 2 Drawing Sheets

PROCESS OF MAKING ALKYL PHOSPHINE COMPOUNDS BY REACTING AN OLEFIN AND A PHOSPHINE IN THE VAPOR PHASE OVER A MINERAL ACID CATALYST

This application is a continuation-in-part of U.S. patent application, Ser. No. 07/728,502 filed Jul. 11, 1991, now abandoned.

BACKGROUND OF THE INVENTION

Major uses of mono-alkylphosphines include uses as chemical intermediates and in semiconductor fabrication. For production of mono-alkylphosphines to be used as chemical intermediates, it is desirable to have a process to make the mono-alkylphosphines in high chemical yield and specificity of mono-alkylated over di-alkylated or tri-alkylated phosphines or other products.

Mono-alkylphosphines, especially mono-tertiary-butylphosphine, are also useful in the manufacture of semiconductor devices such as solar cells and computer chips produced through processes such as metalorganic chemical vapor deposition (MOCVD) and other processes and which require volatile sources of phosphorus as reactants therein. Mono-alkylphosphines for use in semiconductor applications must be of high chemical purity, containing minimum amounts of stereoisomers or other chemical compounds and, especially, substantially no metallic or oxygenating impurities. Use of such very high purity monoalkylphosphines makes possible the fabrication of high quality semiconductor materials without the toxicity and environmental hazards associated with the use of phosphine gas, which has been the typical volatile source of phosphorus used in semiconductor fabrication. Therefore, a process is needed to make very high purity mono-alkylphosphines, containing substantially no metallic or oxygenating impurities.

The production of alkylphosphines typically involves reaction of a Grignard reagent or other organometallic reagent with phosphorus trichloride to produce an alkylated phosphorus halide derivative, which is then converted to the alkylated phosphorus hydride (alkylphosphine) by reaction with such substances as $NaBH_4$, $LiAlH_4$, or $Zn/HCl$.

Alternatively, the appropriate olefin typically has been reacted with phosphine in the liquid phase using either acid or free radical catalysts.

For example, U.S. Pat. No. 2,584,112 discloses a process for the preparation of mono-alkylphosphine by condensing phosphine with an olefin in the presence of a strong non-oxidizing acid catalyst. Noted catalysts include alkyl- and aromatic-sulfonic acids, liquid HF, $F_3CCOOH$, $BF_3$ and $H_3PO_4$—$P_2O_5$.

Hoff, M.C. and Hill, P.(JACS 24 p. 356 (1959)) also disclose phosphine addition to olefins in the liquid phase in the presence of non-oxidizing acids. Mono- and dialkylated products were reported, however, the process required the use of 20–40 atm. pressures.

U.S. Pat. No. 4,922,025 discloses the production of organophosphines over a zeolitic catalyst in an autoclave having high pressures therein. See also W. Hoelderich, et al., Proc. Int. Congress on Catalysis, 9th, 1, 316-22 (1988).

U.S. Pat. No. 4,163,760 discloses a continuous, liquid phase, free radical, catalyzed process for the production of organic phosphines over an azobisisobutyronitrile and reactor pressures of 80–300 bar.

Stiles, A.R. (JACS 84, 3282 (1952)) also discloses the preparation of organophosphines by free radical catalyzed addition of olefins to $PH_3$ through the use of radiation and sensitizers.

Free radical and acid catalyzed additions of olefins to phosphine give different products, which are the result of anti-Markonikov and Markonikov addition, respectively. Thus, free radical catalyzed addition of 2-methyl-1-propene to phosphine produces predominantly mono-iso-butylphosphine, whereas acid catalyzed addition of 2-methyl-1-propene to phosphine produces predominantly mono-tertiary-butylphosphine. Accordingly, the free-radical catalyzed processes are not useful to make mono-tertiary-butylphosphine or other mono-alkylphosphines comprising tertiary carbon-phosphorus linkages.

The methods used in the prior art to carry out acid catalyzed additions of olefins to phosphine, including those noted above, are typically low yield batch processes which require high reaction temperatures and/or high reaction pressures. Use of these processes further requires product purification and involves the generation of waste streams of significant quantities, the recycle or proper disposal of which pose significant problems in the current environment.

It is therefore an object of the present invention to provide a process for the production of alkylphosphines and especially mono-alkyl phosphines by acid catalyzed addition of olefins to phosphine, which may be run in a continuous fashion. It is a further object of the present invention to provide a process which does not involve high reaction pressures. It is still further an object of the present invention to provide a process which produces a high yield of product of relatively high quality, thereby obviating the necessity of costly purification procedures. It is still another object of the invention to provide a process which does not require disposal of significant quantities of reactants and/or byproducts.

SUMMARY OF THE INVENTION

The present invention is directed to the production of alkyl phosphines comprising contacting in the vapor phase an olefin and phosphine over a non-oxidizing acid catalyst.

The present invention is further directed to the production of alkylphosphines in a continuous manner.

The present invention is still further directed to the selective production of mono-alkylphosphines.

DETAILED DESCRIPTION OF THE INVENTION INCLUDING PREFERRED EMBODIMENTS

Figure 1:
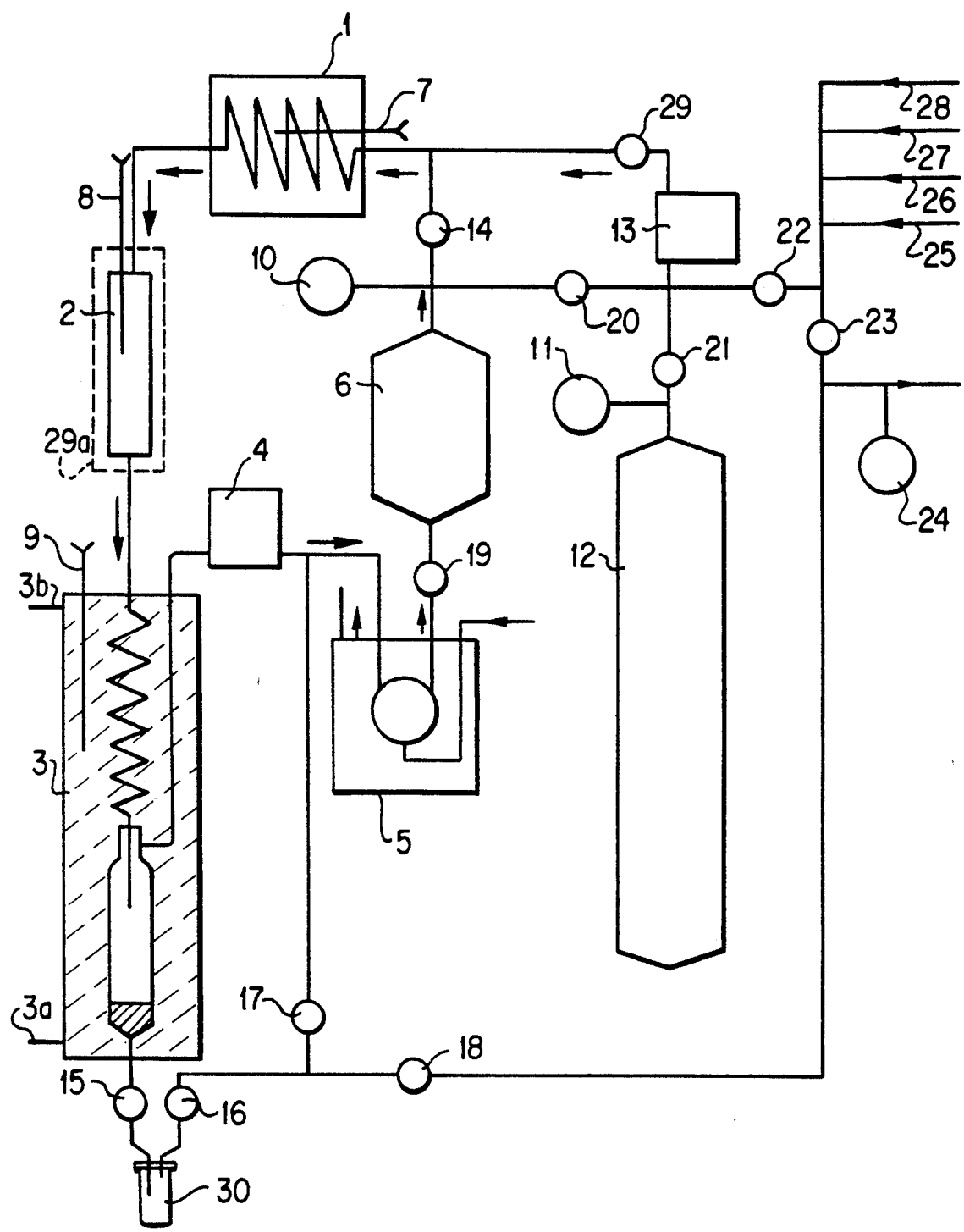
FIG. 1 is a schematic view of apparatus which may be used in the continuous operation of the instant invention.

The term "olefin", as used herein, includes hydrocarbons having a single ethylenic double bond such as normal and branched chain aliphatic olefins, cycloaliphatic olefins, aryl substituted olefins and the like.

Any olefin which can be vaporized, caused to contact a mineral acid catalyst, and thereby be made to react with phosphine, may be used in the present process.

Olefins containing at least three carbon atoms are used in the present process. Olefins containing 3 to about 12 carbon atoms are preferred, while olefins containing from 3 to about 6 carbon atoms are especially preferred.

Normal and branched chain aliphatic olefins preferred for making mono-alkylphosphines according to the invention include, for example, propene, 1-butene, 2-butene, 2-methyl-1-propene, 2-methyl-1-butene, 2,3-dimethyl-1-butene, 2-ethyl-1-butene, 2-methyl-1-pentene, and the like. Mostly preferably, 2-methyl-1-propene is the olefin used in the practice of the present invention.

Cycloaliphatic olefins useful as olefin reactants in the invention include, for example, cyclopentene, cyclohexene, 2-methylcyclopentene, and the like.

The term "phosphine", as used herein, means phosphorus trihydride, $PH_3$ The term "monoalkyl-phosphine", as used herein, means a compound of the formula $R^1PH_2$, wherein $R^1$ is an alkyl or cycloalkyl moiety derived from one of the olefins listed above by Markonikov addition of $PH_3$ to the olefin. The term "dialkylphosphine" as used herein means a compound of the formula $R^1R^2PH$, wherein $R^1$ is as indicated above and $R^2$ is an alkyl moiety having seven carbons or less.

The catalyst used in the present process is a non-oxidizing acid capable of protenating the olefin such as a sulfonic, fluorinated sulfonic, phosphoric, phosphonic, phosphinic, silicic, or arsenic acid.

The catalyst used in the present process may also be a solid molecular acid such as a polymeric acid derivative. Preferred polymeric acids include Amberlyst ® and Nafion ® and the like, sold under said trademarks by Aldrich Chemical Co. Inc.

When the catalyst used in the present process comprises a liquid, non-oxidizing strong acid, such as phosphoric acid, silicic acid, methanesulfonic acid, arsenic acid, or the like, it is used absorbed onto a solid support. Examples of materials used to support non-oxidizing strong acids for use in and the present process include inert materials such as silica, Kieseegudr, montmorillonite and the like.

Preferred catalysts are phosphoric acid, arsenic, and sulfonic acid. Especially preferred is phosphoric acid. As previously mentioned, the catalyst may be present in a solid form. Catalysts such as phosphoric acid are therefore preferably bound to a solid support, such as kieselguhr or silica gel. A suitable phosphoric acid catalyst is commercially available from UOP under the designation UOP-SPA ®. A suitable solid sulfonic acid catalyst is available from Alfa Inorganics Co. under the designation NAFIONH ®.

The catalyst is preferably present in a form which exposes maximum surface area to the reactants. Any suitable form of the acid, alone or on a support, may be used, including extrudates, flakes, pellets, powders, or particles of any shape. Use of catalyst in the form of extrudates is preferred. In the case of the preferred phosphoric acid catalyst, use of 8 to 18 mesh (V.S.) particles has been found to be especially efficient. Catalyst particles of this size have been found to cause only an acceptable pressure drop in the system. Yet, they are of sufficient size to resist migration throughout the system.

If desired, pretreatments of the catalyst may be used to increase selectivity, reactivity, lifetime, and the like of the catalysts used in the present process. For example, in use of the preferred UOP-SPA catalyst mentioned above, it has been found desirable to pretreat the catalyst bed by exposing it to the phosphine-olefin mixture for several hours at about 80C.

The present process is carried out in a continuous mode, so as to enable the production of high yields of high purity mono-alkylphosphines, essentially free of dialkylphosphine by-products.

To conduct the present continuous process, an apparatus is required which comprises a reactor chamber, containing a solid, non-oxidizing, strong acid catalyst, with a means to pass a gaseous phosphine -olefin mixture over the catalyst, and a means to collect alkylphosphine products which are formed.

The type of reactor chamber and catalyst bed used to carry out the present process is not critical. Fixed fluidized, or ebulliated beds may be used.

Reaction temperatures in the range of 15° C. to about 230° C. are used to carry out the present process. Preferred are temperatures from about 60° C. to about 230° C. Optimum reaction temperatures will depend on the olefin used, the type of catalyst, and the type of reactor. If desired, the catalyst bed may be heated to obtain improved selectivity, reactivity or other desirable reaction features. Heating may be accomplished by preheating of the reactants, by use of an auxiliary heater in the reaction vessel or both.

It is not necessary to use high phosphine or olefin pressures in carrying out the present invention. It is only necessary to use pressures high enough to insure a sufficient flow of reactants over the catalyst. Since high pressures of phosphine are not required, it is not necessary to use compressed phosphine gas in the practice of the current invention. Total pressures of phosphine plus olefin of about 0.1 psig to about 25 psig are preferred while pressures ranging from about 10 psig to about 20 psig are especially preferred. Use of total pressures higher than about 25 psig is possible but not necessary, or particularly desirable in the practice of the present invention.

In carrying out the present process, the amount of catalyst used and the residence time of phosphine — olefin reagents in the reactor are not critical. Usually, it is desirable to adjust catalyst volumes and residence times to cause a clean, high one-pass conversion of phosphine — olefin to mono-alkyl-phosphine.

The method of collecting product is not critical. In a preferred collection mode, following contact with the catalyst, the alkylphosphine-containing gas stream is cooled such that the high boiling alkylphosphine products are condensed and thereby removed from the gas stream. Temperatures used in such condensation of product are not critical. It is desirable to use a collection temperature low enough to cause the condensation of mono-alkylphosphine products, but not so low that reactant phosphine and olefin are also condensed. When only mono-alkylphosphines are condensed, purification is simplified and, if desired, recycling of phosphine and olefin reactants is facilitated.

A preferred apparatus in which to conduct the present process comprises a means to circulate a phosphine - olefin mixture of constant composition over a catalyst bed under conditions which cause olefin and phosphine to combine to form alkylphosphine, and a means to condense alkylphosphine which is formed from the mixtures of gases exiting the catalyst chamber, and a means to recycle the unreacted phosphine — olefin mixture. It is preferred to arrange catalyst placement and circulation rate to insure all of the reactant gases make contact with the catalyst in one pass through the catalyst bed. It is further preferred to arrange the condensing system to condense as much of the alkylphosphine product as possible, while not condensing the reactant phosphine - olefin mixture.

In an especially preferred continuous embodiment of the present invention, the apparatus shown in FIG. 1 is used. The apparatus contains a circulation loop comprising a preheater (1), heated reactor chamber (2), refrigerated condenser (3), mass-flow meter / controller (4), circulating pump (5), ballast (6), thermocouples (7), (8), and (9), and pressure gauge (10). The reactant feed system comprises a reservoir (12), pressure gauge (11), mass flow meter / controller (13), feed lines (25) for phosphine, (26) for nitrogen, and (27), (28) for olefins, a line to the vacuum pump (not shown), and a vacuum gauge (24). The product reservoir (30) is connected to the condenser system through valves (15) and (16). Valves (21), (22), (23), (29), (14), (20), (19), and (17) are of the air actuated type. Product is continuously transferred from the condenser (3) to the reservoir (30) through valve (15). The reactor (2) is first charged with catalyst. The entire system is evacuated through valve (23) in order to remove air. The pressure is monitored with vacuum gauge (24). If the preferred solid phosphoric acid catalyst is utilized, it may be preconditioned as described above through its exposure to the reactant gas mixture, circulated using the pump (5), at low temperatures. After preconditioning of the catalyst bed, the preheated reaction gas mixture is introduced to the reactor (2) which is maintained at the process temperature by the reactor oven (29a). The reactor exhaust, which contains the alkylated phosphine products, is then cooled in the condenser (3) in which product condenses and collects at the bottom thereof. The remaining reactant containing gas stream is pumped into the ballast (6) and, subsequently, back to the preheater (1). The pressure in the circulating loop is maintained at a constant level by the continuous injection of makeup reactant gas mixture from the ballast, through mass flow meter controller (13), using valve (29). The circulation rate in the loop is measured and regulated by the mass flow meter / controller (4). Either the reactant gas reservoir (12) or the reactor gas feed lines (25), (26), (27), and (28) can be used to provide the makeup reactant gas mixture.

In formation of mono-tertiary-butylphosphine from phosphine and 2-methyl-1-propene in the continuous reaction mode and apparatus just described, it has been found that mono-tertiary-butylphosphine is obtained in yields exceeding 90 wt. % based on consumed phosphine and 90% based on consumed olefin. The mono-tertiary-butylphosphine obtained contains detectable quantities of di-tertiary-butylphosphine. A second, mono-alkyl-phosphine, derived from addition of the dimer of 2- methyl-1-propene to phosphine, has also been observed under some conditions. The mono- to di-tertiary-butyl-phosphine ratio typically exceeds 10. The-mono-tertiary-butylphosphine which is obtained usually contains some dissolved 2-methyl-1-propene but has only very low levels of germanium, sulfur, metallic, or oxidizing impurities, i.e. less than 1 ppm.

Mono-alkylphosphines and especially mono-tertiary-butylphosphine produced in accordance with the present invention can be used as a volatile source of phosphorus in metalorganic chemical vapor deposition (MOCVD). The use of mono-tertiary-butylphosphine in fabrication of semiconductors by MOCVD is disclosed in published European Patent Application No. 296,257.

A disclosure directed to the MOCVD process may be found in U.S. Pat. Nos. 4,368,098 and 4,404,265, the contents of which are expressly incorporated herein by reference. Semiconductor materials fabricated by the MOCVD technique are typically found to be contaminated with impurities found in gaseous sources used to make them. High purity gaseous sources are thus required, especially gaseous sources which do not contain deleterious amounts of sulfur, germanium, metallic, and oxygenating impurities, all of which impurities adversely affect the electrical properties of semiconductor materials.

Mono-tertiary-butylphosphine obtained by the process of the present invention can be used without lengthy purification to fabricate high quality indium phosphide thin films by MOCVD.

If desired, mono-tertiary-butylphosphine and other mono-alkylphosphines obtained by the process of the present invention can, however, be further purified by distillation. The method of distillation is not critical except that exposure to light and air should be avoided.

The following examples are set forth for purposes of illustration only and are not to be construed as limitations on the present invention except as set forth in the appended claims. All parts and percentages are by weight unless otherwise specified.

EXAMPLE I

The apparatus shown in FIG. 1 is used to produce mono-tertiary-butylphosphine (TBP) as follows. The reactor is charged with 42 parts of UOP-SPA catalyst (8-18 mesh U.S.). The ballast is charged with a 10/1 mole phosphine 2-methyl-1-propene mixture at a total pressure of 15 psig. The catalyst is preconditioned by circulating the gas mixture through the reactor for 2.5 hours, while temperature is maintained in the 40°-80° C. range. With the circulation rate continuing at about 5 L/min., the reactor temperature is then raised to and maintained in the 170°-192° C. range. The reactant gas mixture 1:1 (mole) phosphine/2-methyl-1-propene is injected into the circulation loop at a rate sufficient to maintain the reactor pressure in the 12-15 psig range. After 8.5 hours of operation, the condenser, maintained at 2°-3° C., is found to contain 9.9 parts of mono-tertiary-butylphosphine (92% purity). The crude mono-tertiarybutylphosphine product is determined by gas chromatography to contain approx. 3% di-tertiary-butyl-phosphine. The yield of mono-tertiary-butylphosphine based on 1/1 phosphine/ 2-methyl-1-propene consumed is 98%.

EXAMPLE 2

The apparatus shown in FIG. 1 is used. The reactor is charged with 42 parts of UOP-SPA catalyst (8-18 mesh U.S.). The catalyst is conditioned in the same manner as described in Example 1. With the circulation rate continuing at 5L/min., the reactor temperature is raised to and maintained in the 220°-230° C. range. The reactant gas mixture — 1:1 (mole) phosphine/ 2-methyl-1-propene is injected into the circulation loop at a rate sufficient to maintain the reactor pressure in the 10-18 psig range. Product mono-tertiary-butylphosphine is continuously removed from the circulating gas stream in the condenser which is maintained at 2°-3° C., and which is periodically drained. Crude mono-tertiary-butylphosphine is produced at the rate of 20 parts/hr. (79% purity). The major impurity is found to be 2-methyl-1-propene. The crude mono-tertiary-butylphosphine is determined by gas chromatography to contain approx. 5% of di-tertiary-butylphosphine.

EXAMPLE 3

Figure 2:
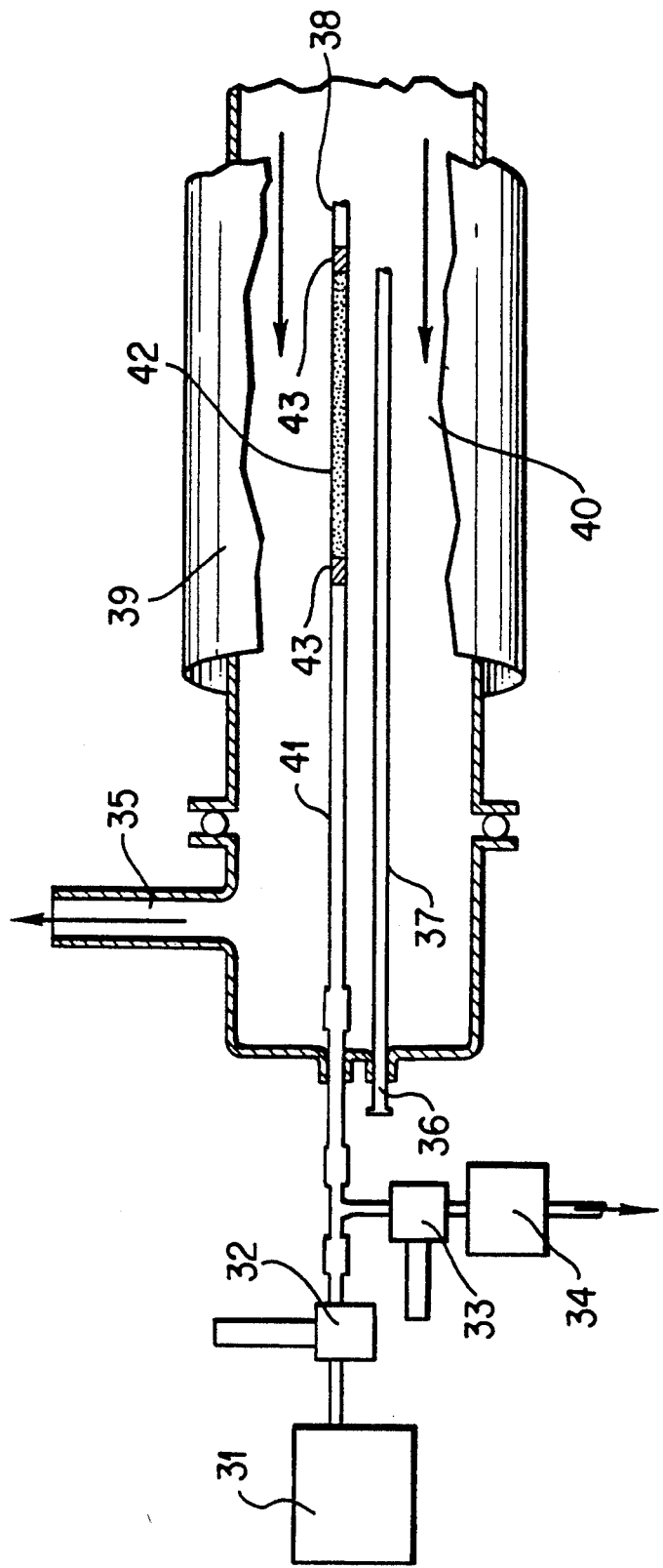
FIG. 2 is a schematic view of a microreactor which may be used in the practice of the instant process such as set forth in Example 1, hereinbelow.

This example is carried out using the microreactor system shown in FIG. 2. The microreactor consists of a 16.5 cm section of a 0.6 cm OD ×4.0 mm ID quartz tube (41) positioned in the center of a 4.0 cm OD ×25. cm quartz tube (40), which is in turn positioned in the center of a microprocessor-controlled resistance-heated tube furnace (39). Tube (38) contains the catalyst (42) held in place by quartz wool plugs (43). It is heated with a microprocessor-controlled 2-zone resistance heater having electrical terminals and thermowell (37). Flow rates through the microprocessor (34) are regulated with a fine metering valve (33) located downstream of the reactor. Flow rates through the reactor are measured with a mass flow meter (not shown) also downstream of the reactor. A mixture of reactant gases (250 sccm) is injected into the large quartz tube through inlet (36). A fraction of the reactant gas flow is then allowed to pass through the microreactor by way of the tube inlet (38). The balance of reactant gases is exhausted through outlet (35). A fraction of the exhaust gas from the microreactor (about 0.3 sscm) is continuously injected into the mass spectrometer (31) through metering valve (32) for analysis of the composition thereof. Exhaust gases are not recirculated. Reactor pressures are maintained at either 200 or 400 Torr. Using the apparatus shown in FIG. 2, and the solid sulfonic acid catalyst Amberlyst ® XN-1010, 2-methyl-1-propene and phosphine are passed through the reactor at partial pressures of 7.7 Torr each, with a total pressure of 200-400 Torr maintained using inert hydrogen carrier gas, at temperatures between ambient and 145° C. Mono-tertiary butylphosphine is detected as the major phosphorus containing product. Formation of 2-methyl-1-propene dimer is also detected under these conditions. The detected ratios of m/e 90 (mono-tertiary-butylphosphine parent peak) to m/e 112 (2-methyl-1-propene dimer parent peak) vary from 0.22 at 200 Torr total pressure and 22° C. reaction temperature, to >20 at 400 Torr total pressure and reactor temperature of 121° C.

EXAMPLE 4

Using the procedure of Example 3 with a different catalyst, Amberlyst ® 15, mono-tertiary-butylphosphine is prepared with >20 selectivity ratio over 2-methyl-1-propene dimer.

EXAMPLE 5

Using the apparatus shown in FIG. 1, and the Amberlyst ® 15 catalyst system, phosphine is reacted with 2-methyl-1-propene to form mono-tertiary-butyl-phosphine, which is detected by gas chromatography. Tertiary-butylmercaptan and di-tertiary butylsulfide are also formed in the reaction.

EXAMPLE 6

The following experiment is conducted, using the apparatus shown in FIG. 1, but without the makeup reservoir (12) so that pressure in the circulation loop decreases as reaction progresses. A total of 42.9 parts of UOP-SPA (8–18 mesh) catalyst is charged in a total reactor volume of 70.8cm$^2$. A reagent mixture of 5:1 phosphine: cis-2-butene is initially charged to the circulating loop of 1.1L volume; a makeup mixture of 3.79L of 1:1 phosphine:cis-2-butene is used. The rate of circulation is approx. 5L/min. In 6hrs. at a reaction temperature of 190°–210° C., a yield of 36.7% of mono-secondary-butylphosphine, based on reaction mixture consumed, is determined by gas chromatography. In a subsequent experiment using the same catalyst charge, at a reactor temperature of 220°–240° C., a 39.4% yield of mono-secondary-butylphosphine is confirmed by gas chromatography.

EXAMPLE 7

Using the apparatus and procedure of Example 6, with propene replacing 2-butene, and a 5:1 phosphine to propene ratio, a 2.0 hour run at a reactor temperature of 180-200C gives 0.54 part of crude product comprising mono-2-propylphosphine and water according to gas chromatography.

EXAMPLE 8

Reaction of phosphine with 2-methyl-1-propene is carried out according to the procedure described in Example 6 except that 24 parts of product are isolated and subjected to weak vacuum. Analysis of the resulting crude product by mass spectrometry indicates that both mono-tertiary-butylphosphine and di-tertiary-butylphosphine are present. The presence of di-tertiary-butylphosphine is further confirmed by $^{31}$P nmr spectroscopy, which reveals $^{31}$P resonances at 77.8 ppm (relative to external H$_3$PO$_4$) (mono-tertiary-butyl-phosphine) and at -20.1 ppm (di-tertiary-butylphosphine, see S.O. Grim, et al. J. Chem Engin. Data 15, 497–99 (1970). The ratio of mono- to di-tertiary-butyl-phosphine in this sample is approximately 28.

EXAMPLE 9

(Comparative Example)

An autoclave is purged with nitrogen prior to introduction of nitrogen purged n-octane and 85% phosphoric acid in a 1.4 / 1 volume ratio to a total volume of about 40% of the autoclave volume. CYPURE ® Electronic Grade phosphine (American Cyanamid Co.) is then introduced to a pressure of 150 psig. The autoclave is then heated to 95° C. with rapid stirring and additional phosphine is added to give a total pressure of 600 psig. 2-Methyl-1-propene is then added under pressure with additional phosphine makeup and heating / cooling to maintain 95° C. and 600 psig over 3 hours. The autoclave is then allowed to cool to ambient temperature and vented to a phosphine destroying means. Several purges with nitrogen are carried out, with venting to a phosphine destroying means. The autoclave contents are then decanted under nitrogen atmosphere and the acid and organic layers are decanted. Organic layers are washed with water and separated from the water which is disposed of. Crude product thus obtained comprises a mixture of octane, 2-methyl-1-propene, phosphine, and mono-tertiary-butyl-phosphine. Distillation of the crude product through a four foot packed column is carried out to remove the remaining phosphine and 2-methyl-1-propene as lights, mono-tertiary-butylphosphine as the main cut, and octane as the heavy fraction. The main cut from the first distillation is redistilled to provide a 20% yield of mono-tertiary-butylphosphine based on consumed phosphine.

EXAMPLES 10-13

Following the procedure of Example 1, various olefins and acid catalysts are employed in replacement of those used therein. The olefins and catalysts are shown in Table I, below. In each case, substantially identical results are achieved with respect to product yield.

TABLE 1

| Example | Olefin | Catalyst |
|---------|--------|----------|
| 10 | 1-butane | Phosphoric acid on Slica Gel |
| 11 | Cyclohexene | Phosphoric acid on Silica Gel |
| 12 | 2,3-dimethyl-1-butene | Arsenic Acid on Montmorillonite |
| 13 | 2-methyl-1-butene | Methane Sulfonic Acid on Kieselguhr |

We claim:

1. A process for the production of an alkylphosphine which comprises continuously reacting an olefin and a phosphine in the vapor phase, at a pressure sufficient to insure flow of the reactants, and in the presence of a solid, non-oxidizing, mineral acid or a liquid, non-oxidizing, mineral acid supported on a solid, inert material, continuously cooling the resultant reaction media so as to condense the resultant alkyl phosphine and recovering the condensed alkyl phosphine in a yield exceeding 90 weight percent based on consumed phosphine and 90 weight percent based on consumed olefin and containing less than 1 ppm of germanium, sulfur, metallic or oxidizing impurities.

2. The process of claim 1 wherein said olefin and phosphine are passed over the supported acid only once.

3. The process of claim 1 wherein said alkyl phosphine is a mono-alkylphosphine.

4. The process of claim 3 wherein the mono-alkylphosphine is mono-t-butyl-phosphine.

5. The process according to claim 1 wherein the olefin and phosphine are recycled and passed over the catalyst a second time.

* * * * *